United States Patent
Fenn et al.

(10) Patent No.: US 9,283,246 B2
(45) Date of Patent: Mar. 15, 2016

(54) PHARMACEUTICAL COMPOSITIONS CONTAINING CARBOXYLATED STARCH

(75) Inventors: Dominik Fenn, Langen (DE); Thomas Schweitzer, Wemmetsweiler (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 337 days.

(21) Appl. No.: 13/606,403

(22) Filed: Sep. 7, 2012

(65) Prior Publication Data

US 2013/0056678 A1 Mar. 7, 2013

Related U.S. Application Data

(60) Provisional application No. 61/531,828, filed on Sep. 7, 2011.

(30) Foreign Application Priority Data

Sep. 7, 2011 (DE) .......................... 10 2011 112 526

(51) Int. Cl.
*A61K 31/718* (2006.01)
*A61K 31/724* (2006.01)
*C08B 31/18* (2006.01)

(52) U.S. Cl.
CPC ............. *A61K 31/724* (2013.01); *A61K 31/718* (2013.01)

(58) Field of Classification Search
CPC ............................... C08B 31/18; A61K 31/718
See application file for complete search history.

(56) References Cited

U.S. PATENT DOCUMENTS

| 4,339,433 | A | 7/1982 | Kartinos et al. | |
|---|---|---|---|---|
| 4,761,237 | A | 8/1988 | Alexander et al. | |
| 6,306,836 | B1 * | 10/2001 | Martis et al. | 514/58 |
| 2004/0014961 | A1 | 1/2004 | Backer et al. | |
| 2004/0152666 | A1 | 8/2004 | Tam et al. | |

FOREIGN PATENT DOCUMENTS

| EP | 1 051 183 | 11/2000 |
|---|---|---|
| EP | 1 131 077 | 9/2006 |
| JP | 8-71146 | 3/1996 |
| JP | 2006 077149 | 3/2006 |
| JP | 2007 230920 | 9/2007 |
| WO | WO 86/00228 | 1/1986 |
| WO | WO 00/33851 | 6/2000 |
| WO | WO 03/035699 | 5/2003 |

OTHER PUBLICATIONS

Tamura et al., Carbohydrate Polymers, 2010, 81, p592-598, Available online Mar. 15, 2010.*
Thaburet et al., Carbohydrate Research, 2001, 330, p21-29.*
Yoon et al. "A General Method for the Synthesis of Cyclodextrinyl Aldehydes and Carboxylic Acids" The Journal of Organic Chemistry, vol. 60, No. 9, May 1, 1995, pp. 2792-2795.
Kuroda et al. "5A,5D-Dicarboxy-β—Cyclodextrin Derivatives—a route for regioselectively difunctionalized Permethyl-β-Cyclodextrin" Tetrahedron Letter, vol. 30, No. 51, Jan. 1, 1989, pp. 7225-7228.
Rousseau et al. "An artificial enzyme that catalyzes hydrolysis of aryl glycosides" Tetrahedrons Letters, vol. 45, No. 47, Nov. 15, 2004, pp. 8709-8711.
Rousseau et al. "Artificial Glydosyl Phosphorylases" Chemistry—A European Journal, vol. 11, No. 17, Aug. 19, 2005, pp. 5094-5101.
Barbier et al. *"Selective TEMPO-Catalyzed Chemicals vs. Electrochemical Oxidation of Carbohydrate Derivatives"* Journal of Carbohydrate Chemistry, vol. 25, Feb. 10, 2006, pp. 253-266.
Heinze et al. "New Polymers Based on Cellulose Lenzinger Berichte" vol. 79, Jan. 1, 2000, pp. 39-44.

* cited by examiner

*Primary Examiner* — Jonathan S Lau
(74) *Attorney, Agent, or Firm* — Jacobson Holman, PLLC.

(57) ABSTRACT

The present invention relates to pharmaceutical compositions containing carboxylated starch derivatives as well a their use as osmotics in particular for use in the treatment of chronic renal failure by dialysis.

Formula I

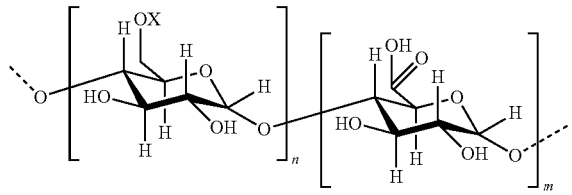

10 Claims, 1 Drawing Sheet

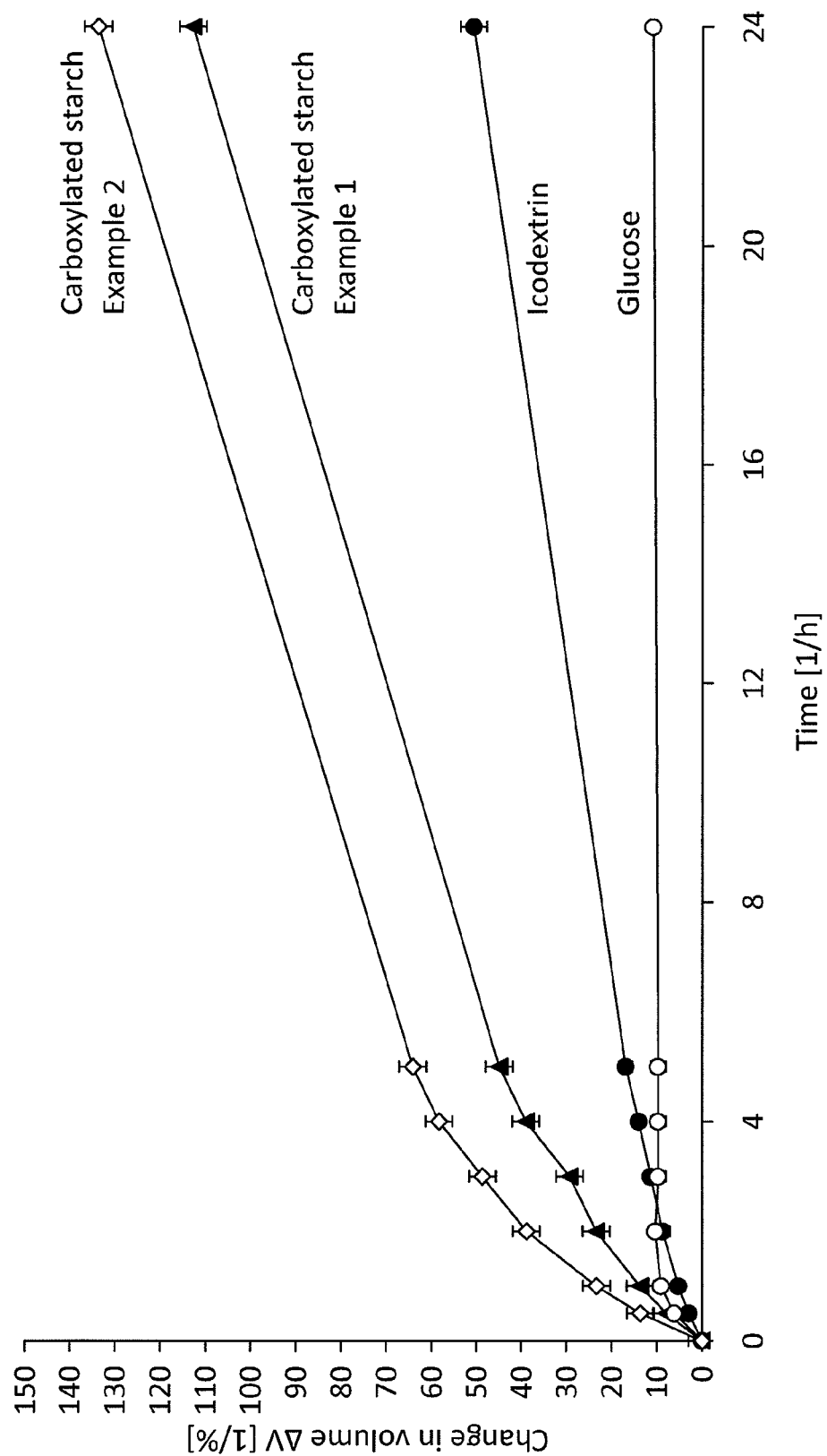

PHARMACEUTICAL COMPOSITIONS CONTAINING CARBOXYLATED STARCH

This is a complete application claiming benefit of provisional 61/531,828, filed Sep. 7, 2011, which has a priority of German no. 10 2011 112 526.8 filed Sep. 9, 2011, hereby incorporated by reference.

The present invention relates to pharmaceutical compositions containing carboxylated starch as well as their use as osmotics, in particular for use in the treatment of chronic renal failure by dialysis.

Osmotically active compounds (osmotics) are used in pharmacy and medicine. For example, osmotics are used to adjust the tonicity of pharmaceutical drugs in particular parenteral medications. In doing so the osmotic pressure of a pharmaceutical drug is adjusted to be hypotonic, hypertonic or isotonic depending on how it is administered. For example, the osmotic pressure of a parenteral medicinal solution may be adjusted to match the osmotic pressure of human blood by adding an osmotic agent (isoosmotic solutions).

Furthermore osmotics are used in the treatment of renal failure by dialysis in particular in hemodialysis or peritoneal dialysis to withdraw excess water from the dialysis patient.

The peritoneal dialysis method is based on the fact that a solution containing osmotically active compounds is introduced into the abdominal cavity of a dialysis patient through a catheter. This solution is left in the patient's abdominal cavity for a certain period of time (usually a few hours) where it manifests its osmotic effect; in other words, endogenous water is withdrawn from the patient into the abdominal cavity. After a certain dwell time, the peritoneal dialysis solution, which is then dilute, is drained out through a catheter.

This principle is used in various methods of peritoneal dialysis treatment. For example, the methods of intermittent peritoneal dialysis (IPD), nocturnal intermittent peritoneal dialysis (NIPD), continuous cyclic peritoneal dialysis (CCPD) or continuous ambulant peritoneal dialysis (CAPD) may be used as needed. Machines which support the patient in performing the peritoneal dialysis method are used in IPD, NIPD and CCPD. CAPD is a manual method.

Adding osmotically active compounds in particular should ensure that the osmotic pressure of the peritoneal dialysis solution is high enough during the entire dwell time in the abdominal cavity to withdraw water from the patient; in other words, water moves from the patient's circulatory system into the abdominal cavity (ultrafiltration).

However, because of the transfer of water into the abdominal cavity, there is necessarily a diluting effect of the peritoneal dialysis solution thereby introduced. This dilution results in a decline in the concentration of the osmotically active compound and thus also in the osmotic pressure of the solution.

If the osmotic pressure of the peritoneal dialysis solution drops due to this dilution effect, this in turn has the result that even the transfer of water to the abdominal cavity per unit of time also drops or may come to a complete standstill. Thus, in these cases, there is no longer an effective withdrawal of water as the dwell time of the peritoneal dialysis solution in the patient's abdominal cavity progresses.

By absorption of osmotically active compounds into the bloodstream of the patient, the direction of the movement of water may even be reversed, i.e., water goes from the abdominal cavity into the patient's blood stream (negative ultrafiltration). This is the case when the dilute peritoneal dialysis solution in the abdominal cavity has a lower osmotic pressure than the endogenous water (for example, the blood) in the patient.

By adding suitable osmotically active compounds to the peritoneal dialysis solution, the osmotic pressure can be maintained over a treatment time suitable for peritoneal dialysis so that there is no excessive decline in ultrafiltration during the dwell time of the solution in the abdominal cavity. This also largely prevents any negative ultrafiltration.

The solutions used in peritoneal dialysis treatment usually contain sugar monomers or polymers, for example, glucose or polyglucose (e.g., starch derivatives) as osmotically active compounds.

U.S. Pat. No. 4,761,237 discloses a peritoneal dialysis solution containing starch hydrolysate glucose polymer with an average degree of polymerization of at least 4.

JP 8071146 relates to a peritoneal dialysis solution containing α- or γ-cyclodextrin, 2-hydroxyethyl ether, 2-hydroxypropyl ether, 6-O-α-glucosyl or 6-O-α-maltosyl derivatives of α-, β- and γ-cyclodextrin.

EP 1 051 183 discloses the use of a glucose polymer consisting of D-sorbitol and D-glucitol and/or gluconic acid for use in peritoneal dialysis.

U.S. Pat. No. 4,339,433 discloses the use of carboxymethyl-polysaccharides as osmotic agents.

WO 86/00228 relates to the use of polyanions and polycations for use in hemodialysis and peritoneal dialysis.

The present invention relates to carboxylated starch and carboxylated starch derivatives of general formula I, wherein n and m are integers greater than or equal to 1 and X is either H or a glucose unit bonded via an α-1,6-glycosidic bond.

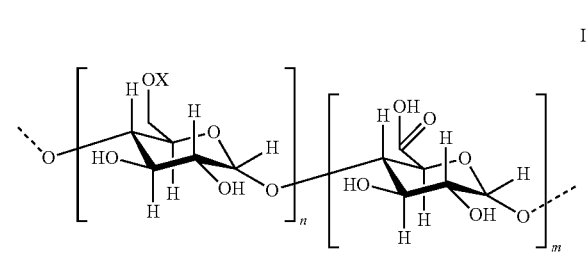

Starch consists of D-glucose units which are linked together by glycosidic bonds. Starch contains approximately 20-30% amylase and approximately 70-80% amylopectin. Amylose consists of linear chains with a helical structure having only α-1,4-glycosidic linkages. Amylopectin consists of branched structures with α-1,4- and α-1,6-glycosidic linkages. After approximately α-1,4-glycosidic linkages, there is a branch via an α-1,6-glycosidic bond. Starch is thus a polymer having predominantly α-1,4-glycosidic linkages. The hydroxyl groups in position $C_6$ are thus predominantly not involved in α-1,6-glycosidic bonds and may be carboxylated. "Predominantly" in this context means at least 85%. This means that at least 85% of the glucose units are bonded to one another exclusively via α-1,4-glycosidic linkages.

One example of a starch derivative is icodextrin. Icodextrin is a water-soluble glucose polymer obtained from starch in which the glucose units are predominantly linked to one another via α-1,4-glycosidic bonds and less than 10% via α-1,6-glycosidic bonds. Icodextrin typically has an average molecular weight of approximately 13,000 to 19,000 Dalton (based on the weight average Mw) and/or approximately 5000 to 6500 Dalton (based on the number average Mn).

The variables m and n of the general formula I are integers greater than or equal to 1. Thus the sum of m+n is greater than or equal to 2. In a preferred embodiment the sum of m+n is preferably greater than 20, particularly preferably 20 to 250, in particular 25 to 150.

The average molecular weight (based on the weight average, Mw) of the inventive carboxylated starch is 5 to 30 kD. In a preferred embodiment, the average molecular weight (Mw) is preferably from 10 to 20 kD, particularly 13 to 19 kD.

The average molecular weight (based on the number average, Mn) of the inventive carboxylated starch is 2 to 12 kD. In a preferred embodiment, the average molecular weight (Mn) is preferably 4 to 8 kD, especially 5 to 7 kD.

Carboxylated starch is obtained, for example, by a method such as that published by T. Heinze et al. for synthesis of carboxylated cellulose (T. Heinze, M. Vieira, U. Heinze; New polymers based on cellulose; Lenzinger Berichte 79 (2000) 39-44).

One object of the present invention is to make available starch derivatives having a high water solubility, an improved osmotic efficacy and an increased ultrafiltration in comparison with starch derivatives of the prior art and which are thus suitable for pharmaceutical compositions in particular for dialysis treatment.

This object is achieved by the subject matter of the patent claims.

The inventive carboxylated starch derivatives are characterized in comparison with the starch derivatives of the prior art by a more uniform substitution pattern, i.e., their structure is more precisely defined (for example, smaller amount of different positional isomers, uniform degree of oxidation).

As a result, unwanted side effects based on the presence of a wide variety of different substitution patterns are largely ruled out. This increases safety for the patient.

In particular the efficacy of the inventive carboxylated starch derivatives may be attributed to defined compounds and is not based on the effects of a complex mixture of a wide variety of different starch derivatives. This also increases safety for the patient and in particular facilitates the evaluation of pharmacological and/or clinical data.

First, mixtures of carboxylated starch derivatives which have a composition that is reproducible only to a limited extent may lead to inadequate reproducibility in obtaining experimental data as is the case, for example, when performing pharmacological or toxicological in vivo or ex vivo experiments and in conducting clinical trials.

The acidic —COOH radical may be deprotonated, i.e., it may be in anionic form and may be present as salts with cations, for example, sodium, potassium, magnesium, calcium, ammonium.

The term "degree of oxidation" in the sense of this description stands for the average number of moles of the —COOH radical, based on one mol glucose units not bonded to another glucose unit by an α-1,6-glycosidic bond. The degree of oxidation may assume values between ≥0 and ≤1. A degree of oxidation of 0 corresponds to unoxidized starch, and a degree of oxidation of 1 means that each glucose unit is oxidized in position 6.

In a preferred embodiment, the degree of oxidation of the inventive carboxylated starch is ≥0.01 and ≥1, preferably between ≥0.05 and ≥0.98, especially preferably between ≥0.1 and ≤0.95.

Preferably a 7.5 wt % aqueous solution of the inventive carboxylated starch derivatives will have a theoretical osmolarity (based on the number average of the molecular weight Mn) of ≥5 mOsm/L, more preferably greater than ≥7.5 mOsm/L, more preferably greater than ≥10 mOsm/L, most preferably greater than ≥12.5 mOsm/L and in particular greater than ≥15 mOsm/L.

For the purpose of this description, the term "theoretical osmolarity" stands for the osmolarity calculated theoretically. Those skilled in the art are familiar with them methods of calculating this value.

In a preferred embodiment, the colloid osmotic pressure of a 7.5 wt % solution of the inventive carboxylated starch derivative is ≥50 mOsm/L or ≥60 mOsm/L, more preferably ≥70 mOsm/L or ≥80 mOsm/L, even more preferably ≥90 mOsm/L or ≥100 mOsm/L, most preferably ≥110 mOsm/L or ≥120 mOsm/L, and in particular ≥130 mOsm/L or ≥140 mOsm/L.

In another preferred embodiment, the colloid osmotic pressure of a 7.5 wt % solution of the inventive carboxylated starch is ≥150 mOsm/L or ≥160 mOsm/mL, more preferably ≥170 mOsm/L or ≥180 mOsm/L, even more preferably ≥190 mOsm/L or ≥00 mOsm/L, most preferably ≥210 mOsm/L or ≥220 mOsm/L and in particular ≥230 mOsm/L or ≥40 mOsm/L.

In another preferred embodiment, the colloid osmotic pressure of a 7.5 wt % solution of the inventive carboxylated starch is 50 to 500 mOsm/L, more preferably 75 mOsm/L to 400 mOsm/L, even more preferably 100 to 300 mOsm/L, most preferably 110 mOsm/L to 275 mOsm/L and in particular 120 mOsm/L to 250 mOsm/L.

In another preferred embodiment, the colloid osmotic pressure of a 7.5 wt % solution of the inventive carboxylated starch is 100 to 500 mOsm/L, more preferably 100 mOsm/L to 400 mOsm/L, even more preferably 100 to 350 mOsm/L, most preferably 100 mOsm/L to 325 mOsm/L and in particular 100 mOsm/L to 290 mOsm/L.

For the purpose of this description the term "colloid osmotic pressure" stands for the experimentally measured osmotic pressure of the solution which is composed of the osmotic pressure and the oncotic pressure. Suitable methods of determining this value experimentally are familiar to those skilled in the art.

The osmolality of the 7.5 wt % aqueous solution of the inventive carboxylated starch is preferably >5 mOsm/kg, more preferably ≥7.5 mOsm/kg, even more preferably ≥10 mOsm/kg, most preferably ≥12 mOsm/kg and in particular ≥15 mOsm/kg.

For the purpose of this description the term "osmolality" stands for the osmolality of the solution determined experimentally by means of the reduction in freezing point. Methods of determining the freezing point reduction are familiar to those skilled in the art.

The osmolarity determined experimentally by means of the reduction in freezing point of a 7.5 wt % aqueous solution of the inventive carboxylated starch derivative is preferably ≥15 mOsm/kg, more preferably ≥17 mOsm/kg, even more preferably ≥19 mOsm/kg, most preferably ≥1 mOsm/kg and in particular ≥23 mOsm/kg.

The inventive carboxylated starch derivatives are preferably suitable as osmotic agents for adjusting the tonicity of pharmaceutical drugs, in particular medicinal solutions for parenteral administration.

In a preferred embodiment, the inventive carboxylated starch derivatives are used in the dialysis treatment, preferably in hemodialysis and/or peritoneal dialysis treatment.

The inventive carboxylated starch derivatives are suitable in particular for use in peritoneal dialysis treatment.

Another subject matter of this invention relates to dialysis solutions containing at least one inventive carboxylated starch or an inventive carboxylated starch derivative.

In a preferred embodiment, the inventive dialysis solution is a hemodialysis solution or a peritoneal dialysis solution. The inventive dialysis solution is in particular a peritoneal dialysis solution.

Dosage forms used in the dialysis treatment are preferably concentrates in multicomponent systems or ready-to-use dialysis solutions.

For the purposes of this invention the term "dialysis solution" comprises a ready-to-use dosage form for the dialysis treatment, i.e., a liquid preparation which is suitable as such for administration. In particular the dialysis solution need not be diluted and/or mixed with other preparations prior to administration.

In contrast with the dialysis solutions described above, concentrates which may be present either in liquid, semisolid or solid form are diluted with water or aqueous solutions prior to administration or they are dissolved in water or aqueous solutions. Similarly the component of a multicomponent system must be mixed together prior to administration in order to obtain a ready-to-use dialysis solution. Concentrates and multicomponent systems may thus be regarded as the precursor of the inventive dialysis solution.

The inventive dialysis solution is preferably a hemodialysis solution or a peritoneal dialysis solution. Hemodialysis and peritoneal dialysis solutions usually contain electrolytes in a concentration which corresponds essentially to the plasma electrolyte concentration. Electrolytes usually include sodium, potassium, calcium, magnesium and chloride ions.

Dialysis solutions usually have a physiologically tolerable pH. This is preferably achieved by using buffers (buffer systems) which may even contribute to the total electrolyte content. The buffers are preferably bicarbonate, lactate or pyruvate.

Furthermore dialysis solutions usually have a physiologically tolerable osmolarity. This is usually achieved by the electrolyte contained in the dialysis solution and inventive carboxylated starch derivatives which are physiologically tolerable as osmotically active compounds (osmotics) in the desired concentration.

The inventive dialysis solution has an osmolarity in the range of preferably 200 to 550 mOsm/L.

In the case when the inventive dialysis solution is a hemodialysis solution, the osmolarity is preferably 200 to 350 mOsm/L or 210 to 340 mOsm/L, more preferably 220 to 330 mOsm/L, even more preferably 230 to 320 mOsm/L, most preferably 240 to 310 mOsm/L and in particular 250 to 300 mOsm/L. Methods of measuring the osmolarity and the osmotic pressure are familiar to those skilled in the art. For example, these may be determined with the help of a membrane osmometer or other suitable measurement methods.

In the case when the inventive dialysis solution is a peritoneal dialysis solution, the osmolarity is preferably 200 to 570 mOsm/L or 210 to 560 mOsm/L, more preferably 220 to 550 mOsm/L, even more preferably 230 to 540 mOsm/L, most preferably 240 to 530 mOsm/L and in particular 250 to 520 mOsm/L. In a preferred embodiment, the osmolarity is 250±50 mOsm/L or 250±45 mOsm/L, more preferably 250±35 mOsm/L, even more preferably 250±25 mOsm/L, most preferably 250±15 mOsm/L and in particular 250±10 mOsm/L. In another preferred embodiment, the osmolarity is 300±50 mOsm/L or 300±45 mOsm/L, more preferably 300±35 mOsm/L, even more preferably 300±25 mOsm/L, most preferably 300±15 mOsm/L and in particular 300±10 mOsm/L. In another preferred embodiment, the osmolarity is 350±50 mOsm/L or 350±45 mOsm/L, more preferably 350±35 mOsm/L, even more preferably 350±25 mOsm/L, most preferably 350±15 mOsm/L and in particular 350±10 mOsm/L. In another preferred embodiment, the osmolarity is 400±50 mOsm/L or 400±45 mOsm/L, more preferably 400±35 mOsm/L, even more preferably 400±25 mOsm/L, most preferably 400±15 mOsm/L and in particular 300[sic]±10 mOsm/L. In another preferred embodiment, the osmolarity is 450±50 mOsm/L or 450±45 mOsm/L, more preferably 450±35 mOsm/L, even more preferably 450±25 mOsm/L, most preferably 450±15 mOsm/L and in particular 450±10 mOsm/L. In another preferred embodiment, the osmolarity is 500±50 mOsm/L or 500±45 mOsm/L, more preferably 500±35 mOsm/L, even more preferably 500±25 mOsm/L, most preferably 500±15 mOsm/L and in particular 500±10 mOsm/L.

The inventive dialysis solution has a pH of preferably 4.0 to 8.0, more preferably from 4.2 to 7.5, even more preferably from 4.4 to 6.8, most preferably from 4.6 to 6.0 or 4.8 to 5.5 and in particular from 5.0 to 5.2 or 5.0±0.1; measured at room temperature (20 to 23° C.). In a preferred embodiment, the pH is 4.8±1.0 or 4.8±0.8, more preferably 4.8±0.7 or 4.8±0.6, even more preferably 4.8±0.5 or 4.8±0.4, most preferably 4.8±0.3 or 4.8±0.2 and in particular 4.8±0.1. In a preferred embodiment, the pH is 5.0±1.0 or 5.0±0.8, more preferably 5.0±0.7 or 5.0±0.6, even more preferably 5.0±0.5 or 5.0±0.4, most preferably 5.0±0.3 or 5.0±0.2 and in particular 5.0±0.1. In a preferred embodiment, the pH is 5.2±1.0 or 5.2±0.8, more preferably 5.2±0.7 or 5.2±0.6, even more preferably 5.2±0.5 or 5.2±0.4, most preferably 5.2±0.3 or 5.2±0.2 and in particular 5.2±0.1. In a preferred embodiment, the pH is 5.5±1.0 or 5.5±0.8, more preferably 5.5±0.7 or 5.5±0.6, even more preferably 5.5±0.5 or 5.5±0.4, most preferably 5.5±0.3 or 5.5±0.2 and in particular 5.5±0.1. In a preferred embodiment, the pH is 6.0±1.0 or 6.0±0.8, more preferably 6.0±0.7 or 6.0±0.6, even more preferably 6.0±0.5 or 6.0±0.4, most preferably 6.0±0.3 or 6.0±0.2 and in particular 6.0±0.1. In a preferred embodiment, the pH is 6.5±1.0 or 6.5±0.8, more preferably 6.5±0.7 or 6.5±0.6, even more preferably 6.5±0.5 or 6.5±0.4, most preferably 6.5±0.3 or 6.5±0.2 and in particular 6.5±0.1. In a preferred embodiment, the pH is 7.0±1.0 or 7.0±0.8, more preferably 7.0±0.7 or 7.0±0.6, even more preferably 7.0±0.5 or 7.0±0.4, most preferably 7.0±0.3 or 7.0±0.2 and in particular 7.0±0.1. In a preferred embodiment, the pH is 7.4±1.0 or 7.4±0.8, more preferably 7.4±0.7 or 7.4±0.6, even more preferably 7.4±0.5 or 7.4±0.4, most preferably 7.4±0.3 or 7.4±0.2 and in particular 7.4±0.1. In a preferred embodiment, the pH is 8.0±1.0 or 8.0±0.8, more preferably 8.0±0.7 or 8.0±0.6, even more preferably 8.0±0.5 or 8.0±0.4, most preferably 8.0±0.3 or 8.0±0.2 and in particular 8.0±0.1.

The inventive dialysis solution contains one or more (e.g., two, three, four or five) inventive carboxylated starch derivatives with different degrees of oxidation, where the inventive carboxylated starch derivatives are defined as given above.

The inventive dialysis solution contains inventive carboxylated starch derivative in a total concentration of preferably 0.001 mM to 10 M or 0.01 to 1.0 M, more preferably 0.10 to 500 mM, even more preferably 1.0 to 250 mM, most preferably 10 to 100 mM and in particular to 90 mM. In a preferred embodiment, the total concentration is 25±24 mM, more preferably 25±20 mM, even more preferably 25±15 mM, most preferably 25±10 mM and in particular 25±5 mM. In another preferred embodiment, the total concentration is 50±25 mM, more preferably 50±20 mM, even more preferably 50±15 mM, most preferably 50±10 mM and in particular 50±5 mM. In another preferred embodiment, the total concentration is 75±25 mM, more preferably 75±20 mM, even more preferably 75±15 mM, most preferably 75±10 mM and in particular 75±5 mM. In another preferred embodiment, the total concentration is 100±25 mM, more preferably 100±20 mM, even more preferably 100±15 mM, most preferably 100±10 mM and in particular 100±5 mM. In another preferred embodiment, the total concentration is 200±25 mM, more preferably 200±20 mM, even more preferably 200±15 mM, most preferably 200±10 mM and in particular 200±5 mM. The total concentration is preferably calculated by means of the average molecular weight of the inventive carboxylated starch derivatives.

The inventive dialysis solution contains inventive carboxylated starch derivative in a total weight concentration of preferably 0.01 g/L to 1.0 kg/L, more preferably from 0.1 to 750 g/L, even more preferably from 1.0 to 500 g/L, most preferably 10 to 250 g/L and in particular from 100 to 200 g/L. In a preferred embodiment, the total weight concentration is 25±24 g/L, more preferably 25±20 g/L, even more preferably 25±15 g/L, most preferably 25±10 g/L and in particular 25±5 g/L. In another preferred embodiment, the total weight concentration is 50±25 g/L, more preferably 50±20 g/L, even more preferably 50±15 g/L, most preferably 50±10 g/L and in particular 50±5 g/L. In another preferred embodiment, the total weight concentration is 75±25 g/L, more preferably 75±20 g/L, even more preferably 75±15 g/L, most preferably 75±10 g/L and in particular 75±5 g/L. In another preferred embodiment, the total weight concentration is 100±25 g/L, more preferably 100±20 g/L, even more preferably 100±15 g/L, most preferably 100±10 g/L and in particular 100±5 g/L. In another preferred embodiment, the total weight concentration is 200±25 g/L, more preferably 200±20 g/L, even more preferably 200±15 g/L, most preferably 200±10 g/L and in particular 200±5 g/L.

The inventive dialysis solution may also contain other osmotically active substances, for example, glucose, polyglucose, crosslinked glucose or polyglucose, mannitol or glycerol.

The inventive dialysis solution preferably contains one or more electrolytes.

The term "electrolyte" in the sense of this invention stands for a substance containing free ions and having electrical conductivity. The electrolyte preferably dissociates completely into cations and anions without making any significant change in the pH of an aqueous composition. This property differentiates electrolytes from buffer substances. The electrolytes are preferably present in a concentration which results in essentially complete dissociation in water.

Preferred electrolytes are selected from the group of alkali metals such as $Na^+$ and $K^+$ and the alkaline earth metals such as $Ca^{2+}$ and $Mg^{2+}$. $Cl^-$ is a preferred anion.

The inventive dialysis solution that contains additional anions, for example, bicarbonate, dihydrogen phosphate, hydrogen phosphate, phosphate, acetate, lactate and pyruvate; however, these anions (in suitable combinations with cations) are not referred to as electrolytes within the sense of the present invention but instead are referred to as buffers because of their buffering capacity.

In a preferred embodiment, the inventive dialysis solution contains $Na^+$ ions. The concentration of $Na^+$ ions is preferably 10 to 200 mM or 50 to 190 mM, more preferably 100 to 180 mM or 110 to 170 mM, even more preferably 115 to 165 mM or 120 to 160 mM, most preferably 125 to 155 mM and in particular 130 to 150 mM. In another preferred embodiment, the inventive dialysis solution does not contain any $Na^+$ ions.

In a preferred embodiment, the inventive dialysis solution contains $K^+$ ions. The concentration of $K^+$ ions is preferably 0.10 to 20 mM, more preferably 0.25 to mM, even more preferably 0.50 to 10 mM, most preferably 0.75 to 7.5 mM and in particular 1.0 to 5.0 mM. In another preferred embodiment, the concentration of $K^+$ ions is 1.0±0.75, 2.0±0.75, 3.0±0.75, 4.0±0.75 or 5.0±0.75 mM and in particular 1.0±0.50, 2.0±0.50, 3.0±0.50, 4.0±0.50 or 5.0±0.50. In another preferred embodiment, the inventive dialysis solution does not contain any $K^+$ ions.

In a preferred embodiment, the inventive dialysis solution contains $Ca^{2+}$ ions. The concentration of $Ca^{2+}$ ions is preferably 0.1 to 3 mM, more preferably 0.25 to 2.75 mM, even more preferably 0.5 to 2.5 mM, most preferably 0.75 to 2.25 mM and in particular 1 to 2 mM. In another preferred embodiment, the concentration of $Ca^{2+}$ ions is 0.25, 0.5, 0.75, 1, 1.25, 1.5, 1.75 or 2 mM. In another preferred embodiment, the inventive dialysis solution does not contain any $Ca^{2+}$ ions.

In a preferred embodiment, the inventive dialysis solution contains $Mg^{2+}$ ions. The concentration of $Mg^{2+}$ ions is preferably 0.01 to 1 mM, more preferably 0.05 to 0.75 mM, even more preferably 0.1 to 0.5 mM, most preferably 0.15 to 0.4 mM and in particular 0.2 to 0.3 mM. In another preferred embodiment, the concentration of $Mg^{2+}$ ions is 0.05, 0.075, 0.1, 0.2, 0.25, 0.50 or 0.75 mM. In another preferred embodiment, the inventive dialysis solution does not contain any $Mg^{2+}$ ions.

In a preferred embodiment, the inventive dialysis solution contains $Cl^-$ ions. The concentration of $Cl^-$ ions is preferably 10 to 300 mM, more preferably 25 to 250 mM, even more preferably 50 to 200 mM, most preferably 75 to 150 mM and in particular 80 to 125 mM.

In another preferred embodiment, the concentration of $Cl^-$ ions is 100±50 mM, more preferably 100±25 mM, most preferably 100±10 mM and in particular 96±4 mM. In another preferred embodiment, the inventive dialysis solution does not contain any $Cl^-$ ions.

The inventive dialysis solution preferably contains one or more buffers.

Suitable buffers are familiar to those skilled in the art. Buffers usually include lactate, bicarbonate, carbonate, dihydrogen phosphate, hydrogen phosphate, phosphate, pyruvate, citrate, isocitrate, succinate, fumarate, acetate and lactate salts. Those skilled in the art know that the corresponding cation of the aforementioned anions is a component of the buffer which is used to adjust the pH (e.g., $Na^+$ as a component of the buffer $NaHCO_3$). However, if the buffer salt has dissociated in water it also has the effect of an electrolyte. For the purposes of this description the concentrations of cations or anions and the total concentration of anions are calculated regardless of whether they are used as component of electrolytes, buffers or other compounds (e.g., as salts of the inventive carboxylated starch derivatives).

In a preferred embodiment, the buffer contains bicarbonate. Bicarbonate is a well-tolerated buffer system, which is in equilibrium with carbonate in an alkaline medium and is in equilibrium with $H_2CO_3$ or $CO_2$ in an acidic medium. Other buffer systems may also be used in addition to bicarbonate if they have a buffering effect in the pH range of pH 4 to pH 8, more preferably in the range of pH 5 to pH 7.6 and in particular in the range of pH 7.6, 7.4, 7.2 and/or 7.0; for example, this also includes compounds such as lactate or pyruvate that can be metabolized to bicarbonate in the body.

In another preferred embodiment, the buffer contains the salt of a weak acid preferably lactate. The acid strength (pKs) of the weak acid is preferably 5. The buffer may also be a mixture of substances having a buffering effect, e.g., a mixture containing bicarbonate and a salt of a weak acid (e.g., lactate). A low bicarbonate concentration has the advantage that the $CO_2$ pressure in the container is low.

In a preferred embodiment, the inventive dialysis solution is buffered by bicarbonate. The bicarbonate concentration is preferably 1.0 to 200 mM, more preferably 2.5 to 150 mM, even more preferably 5 to 100 mM, most preferably 5 to 75 mM or 10 to 50 mM and in particular 20 to 30 mM. In another preferred embodiment, the bicarbonate concentration is 25 mM. In another preferably embodiment the inventive dialysis solution contains no bicarbonate.

In a preferred embodiment, the inventive dialysis solution is buffered by lactate. The lactate concentration is preferably 1.0 to 200 mM, more preferably 2.5 to 150 mM, even more preferably 5 to 100 mM, most preferably 10 to 50 mM or 10 to 25 mM and in particular 15 mM. In another preferred embodiment, the inventive dialysis solution contains no lactate.

In a preferred embodiment, the inventive dialysis solution is buffered by acetate. The acetate concentration is preferably 1.0 to 100 mM, more preferably 1.0 to 50 mM, even more preferably 1.0 to 25 mM, most preferably 1.0 to 10 mM or 2.0 to 7.5 mM and in particular 2.5 to 7.0 mM. In another preferred embodiment, the inventive dialysis solution contains no acetate.

The total volume of dialysis solution is not limited. The volume usually amounts to several liters (suitable administration volume for one patient) up to a few hundred liters (suitable supply volume for more than one patient).

As already explained above, the term "dialysis solution" in the sense of this invention is to be understood to refer to a ready-to-use dialysis solution, i.e., the dialysis solution may be used directly for the dialysis treatment (hemodialysis or peritoneal dialysis).

In a preferred embodiment, the inventive dialysis solution is a peritoneal dialysis solution as described below.

The peritoneal dialysis solution is biochemically formulated so that it essentially corrects the metabolic acidosis condition associated with renal failure. The peritoneal dialysis solution preferably contains bicarbonate in approximately physiological concentrations. In a preferred embodiment, the peritoneal dialysis solution contains bicarbonate in a concentration of approximately 20 to 30 mM. In another preferred embodiment, the peritoneal dialysis solution contains a bicarbonate concentration of 25 mM.

Furthermore the peritoneal dialysis solution preferably contains carbon dioxide with a partial pressure ($p_{CO_2}$) of less than 60 mmHg. In a preferred embodiment, the $p_{CO_2}$ of the peritoneal dialysis solution is essentially equal to the $p_{CO_2}$ measured in blood vessels.

Furthermore the peritoneal dialysis solution preferably has a pH of approximately 7.4. Therefore the peritoneal dialysis solution is a physiologically tolerable solution.

The peritoneal dialysis solution preferably contains a weak acid with a pKs ≤5. The weak acids are preferably compounds which occur as physiological metabolites in the glucose metabolism. The weak acid is preferably selected from the group consisting of lactate, pyruvate, citrate, isocitrate, ketoglutarate, succinate, fumarate, malate and oxaloacetate. These acids may either be present alone or as a mixture in the peritoneal dialysis solution. The weak acids are preferably present in a concentration of 10 to 20 mEq/L and essentially as sodium salts in the peritoneal dialysis solution. The weak acid is preferably present in the peritoneal dialysis solution in an amount corresponding to the daily metabolic hydrogen production of approximately 1 mEq/kg per day.

The peritoneal dialysis solution contains at least one inventive carboxylated starch or an inventive carboxylated starch derivative as defined above.

The inventive peritoneal dialysis solution preferably has a bicarbonate concentration and a $p_{CO_2}$ like those measured in healthy patients not in renal failure. The weak acid diffuses along the concentration gradient from the dialysis solution into the blood of the dialysis patient and thus corrects the metabolic acidosis of the dialysis patient.

Another subject matter of this invention relates to multi-component systems for preparing the ready-to-use dialysis solutions described above. The preparation preferably takes place in a manner which is described in detail, i.e., by following a corresponding instruction (protocol). Said preparation may be performed manually, e.g., by mixing individual components or diluting one component with water. However, the preparation may also take place in an automated fashion, e.g., by means of an apparatus which is suitable for this process and may be commercially available. The preparation need not necessarily lead to a dialysis solution with a static (uniform) composition but instead may also lead to a dialysis solution which undergoes a continuous change in its composition, and this change can be monitored by a suitable device. For example, the inventive carboxylated starch may be present in a dialysis solution, which is diluted continuously during the dialysis treatment, so that the patient is exposed to a decreasing concentration of carboxylated starch.

In a preferred embodiment, the inventive dialysis solutions are suitable for use in the treatment of renal failure.

In another preferred embodiment, the inventive dialysis solutions are suitable for use in dialysis treatment.

In another preferred embodiment, the inventive dialysis solutions are suitable for use in hemodialysis and/or peritoneal dialysis treatment.

Another subject matter of this invention relates to a kit which is configured for preparing the inventive dialysis solutions, such that the kit comprises
  a first component,
  a second component, and
  optionally an additional component or several additional
    components, and
the inventive dialysis solution is prepared by mixing the first component with the second component and optionally the additional component(s).

The kit comprises at least one first component and one second component. The kit may also comprise additional components, for example, a third component and a fourth component. The kit preferably consists of two components, which are preferably different from one another.

In the sense of this invention the term "component" preferably comprises liquid, semisolid or solid compositions which may be the same as one another or different from one another, such that by mixing all the components of the kits, the inventive ready-to-use dialysis solution is obtained. An individual component preferably contains part of the ingredients which are contained in the ready-to-use dialysis solution.

The first and second components may independently of one another be solid, semisolid or liquid. In the case when the components are liquid, they may be solutions or dispersions (e.g., dispersions or suspensions).

In a preferred embodiment, the first component is liquid, preferably pure water or an aqueous solution, and the second component is also liquid. In another preferred embodiment, the first component is liquid preferably pure water or an aqueous solution and the second component is solid preferably a powdered mixture.

The first component is preferably a solution containing osmotically active substances (e.g., inventive carboxylated starch derivatives), calcium ions, magnesium ions, hydronium ions and chloride ions.

The inventive kit may be embodied in various ways. For example, the individual components may be present in separate containers (e.g., individual bags). However, the inventive kit is preferably a container, for example, a multichamber container system (e.g., flexible or rigid multichamber contain system), preferably a flexible multichamber bag system.

The inventive kit is preferably a multichamber container system which contains the first component, the second component and optionally one or more additional components in chambers which are separated from one another by soluble and/or breakable separation systems (e.g., breakable dividing parts) such that the first component, the second component and optionally the one or more additional components can be mixed together with one another after dissolving and/or breaking the separation system in order to obtain the inventive dialysis solution.

The multichamber container may be in the form of a plastic container (e.g., a multichamber plastic bag) comprising a separate chamber for each individual component. The plastic container preferably holds the individual component solutions in chambers, each being separated from the others by dividing elements.

The multichamber container is preferably a two-chamber bag comprising a plastic container with a first chamber and a second chamber, where the chambers are separated from one another by a soluble and/or breakable dividing system, and the first chamber holds the first component and the second chamber holds the second component. Releasing and/or breaking of the dividing system leads to mixing of the two components and results in the ready-to-use dialysis solution. The first chamber and the second chamber are preferably arranged adjacent to one another in the container and are separated from one another by the dividing system. The dividing system is preferably a dividing seam (e.g., a soluble or breakable weld). The dividing seam is preferably opened by applying a pressure to one of the chambers whereupon the dividing seam breaks or dissolves and the contents of the two chambers become mixed and the mixture may be used as a ready-to-use dialysis solution in the dialysis treatment.

The first component of the inventive kit is preferably a sterile solution containing an acid and having a pH of ≤6.0; the second component is preferably also a sterile solution, preferably containing a buffer and having a pH ≥7.0.

The inventive carboxylated starch derivatives may be contained in the first component or in the second component as well as in both components in the same or different concentrations. In a preferred embodiment, the inventive carboxylated starch is contained only in the first (acidic) component. In another preferred embodiment, the inventive carboxylated starch derivative is contained only in the second (basic) component. The first component and/or the second component and/or the optional additional component(s) may contain one or more electrolytes or also buffers.

Those skilled in the art will recognize that mixing the individual components usually involves a dilution effect for the case when the components contain the ingredients in different concentrations. For example, if the inventive carboxylated starch derivatives are contained exclusively in one of the components, mixing these components with at least one other component will lead to an increase in the volume with respect to the amount of the inventive carboxylated starch derivatives present and thus will result in a dilution effect, i.e., a decline in the concentration of carboxylated starch derivatives; consequently the components will preferably contain the inventive carboxylated starch derivatives in a higher concentration than the ready-to-use dialysis solution.

The concentration of inventive carboxylated starch or inventive carboxylated starch derivatives in the component is preferably close to the saturation concentration at a temperature of 5° C. in order to ensure adequate stability in storage at higher temperatures.

In a preferred embodiment, the total weight concentration of inventive carboxylated starch or starch derivatives in the component is 0.01 g/L to 1.0 kg/L, more preferably 0.1 to 750 g/L, even more preferably 1.0 to 500 g/L, most preferably 10 to 250 g/L and in particular 100 to 200 g/L. In another preferred embodiment, the total weight concentration of inventive carboxylated starch or starch derivatives in the component is 25±24 g/L, g/L, more preferably 25±20 g/L, even more preferably 25±15 g/L, most preferably 25±10 g/L and in particular 25±5 g/L. In another preferred embodiment, the total weight concentration of inventive carboxylated starch or starch derivatives in the component is 50±25 g/L, more preferably 50±20 g/L, even more preferably 50±15 g/L, most preferably 50±10 g/L and in particular 50±5 g/L. In another preferred embodiment, the total weight concentration of inventive carboxylated starch or starch derivatives in the component is 75±25 g/L, more preferably 75±20 g/L, even more preferably 75±15 g/L, most preferably 75±10 g/L and in particular 75±5 g/L. In another preferred embodiment, the total weight concentration of inventive carboxylated starch or starch derivatives in the component is 100±25 g/L, more preferably 100±20 g/L, even more preferably 100±15 g/L, most preferably 100±10 g/L and in particular 100±5 g/L. In another preferred embodiment, the total weight concentration of inventive carboxylated starch or starch derivatives in the component is 200±25 g/L, more preferably 200±20 g/L, even more preferably 200±15 g/L, most preferably 200±10 g/L and in particular 200±5 g/L.

In a preferred embodiment, the second component contains the total amount of inventive carboxylated starch or inventive starch derivatives and a suitable buffer which adjusts the pH of the second component to more than 7.0, more preferably to more than 7.5, even more preferably to more than 8.0, most preferably more than 8.5 and in particular more than 9.0. This may preferably be achieved by bicarbonate which may be present, for example, in the form of dissociated sodium bicarbonate and/or potassium bicarbonate. In another preferred embodiment, the second component is solid and comprises a powdered mixture containing at least one inventive carboxylated starch or at least one inventive carboxylated starch derivative and at least one buffer, e.g., sodium and/or potassium bicarbonate.

The multichamber bag is preferably suitable for producing a dialysis solution which can be used in the peritoneal dialysis treatment and preferably contains the following ingredients in the following concentrations:

| | |
|---|---|
| $Ca^{2+}$ | 0.5 to 5 mEq/L; |
| $Mg^{2+}$ | 0 to 3.0 mEq/L; |
| $Cl^-$ | 90.5 to 121 mEq/L; |
| $K^+$ | 0 to 4.0 mEq/L; |
| $HCO_3^-$ | 25 to 40 mEq/L; | wherein
a chamber of the multichamber bag system contains a first acid concentrate and another chamber contains a second basic concentrate such that the acid concentrate contains $Ca^{2+}$ ions and the basic concentrate contains $HCO_3^-$ ions but no $Ca^{2+}$ ions; and the two concentrates can be mixed with one another after dissolving and/or breaking the dividing system (e.g., dividing seam) such that the mixing of the two concentrates leads to the preparation of the ready-to-use dialysis solution and the pH of the ready-to-use dialysis solution is 7.0 to 7.6.

The basic concentrate preferably contains at least one inventive carboxylated starch or at least one inventive carboxylated starch derivative and optionally glucose and/or polyglucose, whereas the acid concentrate does not contain any inventive carboxylated starch or starch derivative and no glucose and/or polyglucose.

The basic concentrate preferably contains a quantity of bicarbonate which leads to a bicarbonate concentration of the ready-to-use dialysis solution of at least 20 mM. The bicarbonate concentration of the basic component is preferably so high that the ready-to-use dialysis solution has a bicarbonate concentration of 25 mM.

The pH of the basic buffered second concentrate is preferably adjusted with hydrochloric acid.

The two concentrates are preferably mixed together in a volume ratio of 10:1 to 1:10 or 8:1 to 1:8, more preferably 5:1 to 1:5 or 3:1 to 1:3, even more preferably 2:1 to 1:2 and in particular 1:1.

The multichamber bag preferably has a gas barrier film which prevents gaseous $CO_2$ from escaping from the system. Those skilled in the art are familiar with gas barrier films.

A preferred subject matter of this invention relates to a method for preparing a dialysis solution in which the desired mixing ratio is automatically achieved by a dialysis machine or a peritoneal dialysis cycler.

In a preferred embodiment, the invention relates to a solid composition which is suitable for preparing the inventive dialysis solution by dissolving in a defined volume of a solvent (e.g., water). The solid composition is preferably a component as described above and is thus a component of the inventive kit. The solid composition contains the inventive carboxylated starch or carboxylated starch derivatives in any solid form, e.g., as a powder, granules, pellets, etc. The inventive carboxylated starch derivatives or the carboxylated starch may be present in spray-dried form or as a lyophilizate.

The inventive solid composition preferably contains a bicarbonate salt such as, for example, sodium or potassium bicarbonate. The substance quantity ratio of bicarbonate to inventive carboxylated starch or the carboxylated starch derivatives in the solid composition is preferably 1:100 to 100:1, more preferably 1:50 to 50:1, even more preferably 1:25 to 25:1, most preferably 1:10 to 10:1 and in particular 1:5 to 5:1.

The defined volume of solvent needed for preparing the inventive dialysis solution by dissolving the solid composition is preferably 1.0 to 2000 L. The solvent is preferably purified water, sterilized water or water for injection purposes which optionally contains one or more of the electrolytes described above, one or more osmotically active substance (e.g., at least one inventive carboxylated starch or starch derivative) and/or one or more of the buffers described above.

Another subject matter of this invention relates to the use of at least one inventive carboxylated starch or at least one inventive carboxylated starch derivative for preparing the inventive dialysis solution (hemodialysis solution or peritoneal dialysis solution).

Another subject matter of this invention relates to the use of an inventive kit for preparing the inventive dialysis solution (hemodialysis solution or peritoneal dialysis solution).

Another subject matter of this invention relates to the use of an inventive solid composition for preparing the inventive dialysis solution (hemodialysis solution or peritoneal dialysis solution).

EXAMPLES

The compounds of examples 1 and 2 were prepared according to a procedure by T. Heinze et al. (T. Heinze, M. Vieira, U. Heinze; New polymers based on cellulose; Lenzinger Berichte 79 (2000) 39-44). The analysis of the samples was performed by using gel permeation chromatography (GPC), $^{13}C$-NMR and FTIR spectroscopy, elemental analysis and conductometric titration. The icodextrin used has a molecular weight of approximately 5800 g/mol according to GPC measurements (based on the number average, Mn) and/or approximately 16,000 g/mol (based on the weight average Mw).

Example 1

One after the other 50 g (0.309 mol) icodextrin, 0.41 g TEMPO (2,2,6,6-tetramethyl-1-piperidinyloxyl radical, $2.63 \cdot 10^{-3}$ mol corresponding to $8.5 \cdot 10^{-3}$ mol/mol AGU) and 2.86 g NaBr (0.02781 mol corresponding to 0.09 mol/mol AGU) were stirred into 3 liters distilled water. The mixture was then cooled in an ice bath to approximately 1° C. The mixture had a pH of 5. Next 85 mL of a 10 wt % NaOCl solution was added slowly by drops while stirring. The procedure was as follows: at first enough solution was added by drops until a pH of 10.8 had been reached. The pH of the mixture was then monitored further. As soon as the pH dropped below 10.8, further NaOCl solution was added slowly by drops. After 1 hour a clear solution was obtained. The carboxylated starch was precipitated stirring the solution into 10 liters of ethanol, then filtered, washed with ethanol/water (v/v=8/2) and dried in vacuo at 50° C.

Yield 50 g

Degree of oxidation (DO, determined by conductometric titration): 0.21

Example 2

One after the other, 50 g (0.309 mol) icodextrin, 0.41 g TEMPO (2,2,6,6-tetramethyl-1-piperidinyloxyl radical, $2.63 \cdot 10^{-3}$ mol, corresponding to $8.5 \cdot 10^{-3}$ mol/mol AGU) and 2.86 g NaBr (0.02781 mol corresponding to 0.09 mol/mol AGU) were stirred into 3 liters distilled water. The mixture was then cooled in an ice bath to approximately 1° C. The mixture had a pH of 5. Next 640 mL of a 10 wt % NaOCl solution was added slowly by drops while stirring. The procedure was as follows: at first enough solution was added by drops until a pH of 10.8 had been reached. The pH of the mixture was then monitored further. As soon as the pH dropped below 10.8, further NaOCl solution was added slowly by drops. After 1 hour a clear solution was obtained. The carboxylated starch was precipitated stirring the solution into 10 liters of ethanol, then filtered, washed with ethanol/water (v/v=8/2) and dried in vacuo at 50° C.

Yield 50 g

Degree of oxidation (DO, determined by conductometric titration): 0.83

Example 3

In a comparative test the osmotic activity of the carboxylated starch derivatives from Examples 1 and 2 of untreated icodextrin was investigated.

For the comparative test a filling volume of 10 mL of an osmotic agent in a concentration of 5% (m/m) in a test solution containing 1 mmol/L $Ca^{2+}$, 0.5 mmol/L $Mg^{2+}$, 138 mmol/L $Na^+$, 106 mmol/L $Cl^-$ and 35 mmol/L lactate was poured into a semipermeable tube (regenerated cellulose, molecular weight cut off (MWCO): 1000 Dalton, Roth) and stored in a bath of the same test solution for 24 hours with movement at a temperature of 38° C. At various times the increase in the filling volume of the tube was determined, which reflected the osmotic effect of the agent.

The results of the comparative test are depicted in FIG. 1 as a diagram.

With the carboxylated starches according to Examples 1 and 2, the increase in volume after 24 hours amounted to 113% and 134% respectively whereas with icodextrin it was 51% and with glucose it was only 11%. The carboxylated starches according to Examples 1 and 2 thus have a stronger osmotic effect than glucose or icodextrin.

The invention claimed is:

1. A pharmaceutical or medical dialysis solution containing at least one carboxylated starch derivative of the general structure I

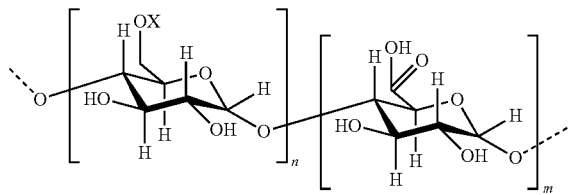

wherein X denotes either H or a glucose unit, n and m are integers greater than or equal to 1 and the degree of oxidation, based on the COOH radical, is between ≥0.0001 and ≤1.

2. The dialysis solution according to claim 1, wherein the degree of oxidation is between ≥0.01 and ≤1.

3. The dialysis solution according to claim 1, wherein the degree of oxidation is between 0.05 and 0.98.

4. The dialysis solution according to claim 1, wherein a 7.5 wt % aqueous solution of the carboxylated starch has an osmolarity of ≥3 mOsm/L.

5. The dialysis solution according to claim 1, for use in the treatment of chronic renal failure by dialysis, preferably hemodialysis or peritoneal dialysis.

6. A kit configured for preparing the dialysis solution according to claim 1, comprising
   a first component,
   a second component, and
   optionally one or more additional components,
wherein by mixing the first component with the second component and optionally with the additional component(s), said dialysis solution is obtained.

7. A solid composition suitable for preparing the dialysis solution according to claim 1, wherein the dialysis solution is obtained by dissolving the solid composition in a solvent.

8. A method comprising dissolving in a solvent at least one carboxylated starch derivative of the general structure I

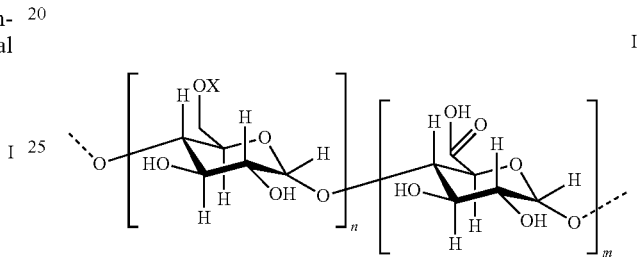

wherein X denotes either H or a glucose unit, n and m are integers greater than or equal to 1 and the degree of oxidation, based on the COOH radical, is between ≥0.0001 and ≤1,
for preparing a dialysis solution according to claim 1.

9. A method comprising mixing together the components of a kit according to claim 6 for preparing a pharmaceutical or medical dialysis solution.

10. A method comprising dissolving in a solvent a solid composition according to claim 7 for preparing a pharmaceutical or medical dialysis solution.

* * * * *